(12) United States Patent
Corelli et al.

(10) Patent No.: US 12,358,919 B2
(45) Date of Patent: Jul. 15, 2025

(54) ANTIBACTERIAL COMPOUNDS

(71) Applicant: Universita' degli Studi di Siena, Siena (IT)

(72) Inventors: Federico Corelli, Siena (IT); Antonella Brizzi, Siena (IT); Claudia Mugnaini, Siena (IT); Jean-Denis Docquier, Siena (IT); Filomena Sannio, Siena (IT)

(73) Assignee: Universita' degli Studi di Siena, Siena (IT)

( * ) Notice: Subject to any disclaimer, the term of this patent is extended or adjusted under 35 U.S.C. 154(b) by 707 days.

(21) Appl. No.: 17/614,388

(22) PCT Filed: Jun. 4, 2020

(86) PCT No.: PCT/IB2020/055270
§ 371 (c)(1),
(2) Date: Nov. 26, 2021

(87) PCT Pub. No.: WO2020/245759
PCT Pub. Date: Dec. 10, 2020

(65) Prior Publication Data
US 2022/0235059 A1    Jul. 28, 2022

(30) Foreign Application Priority Data
Jun. 5, 2019 (IT) .................. 102019000008151

(51) Int. Cl.
C07D 487/04 (2006.01)
(52) U.S. Cl.
CPC ................ C07D 487/04 (2013.01)
(58) Field of Classification Search
CPC .................................. C07D 487/04
See application file for complete search history.

(56) References Cited

FOREIGN PATENT DOCUMENTS

| WO | 1994005649 A1 | 3/1994 |
| WO | 2008014307 A2 | 1/2008 |

OTHER PUBLICATIONS

Russell, Front Immunol. 2011, 2, 53 (Year: 2011).*
Search Report and Written Opinion of PCT/IB2020/055270 of Nov. 20, 2020.

* cited by examiner

*Primary Examiner* — Layla D Berry
*Assistant Examiner* — Sarah Grace Scrivener
(74) *Attorney, Agent, or Firm* — Silvia Salvadori, P.C.; Silvia Salvadori

(57) ABSTRACT

The present invention relates to compounds of formula (I) their salts and derivatives. Further object of the present invention are compositions, which comprise at least one compound of formula (I) or its pharmaceutically acceptable salts and derivatives and excipients and, optionally, a further active compound. Further object of the present invention are compounds of formula (I) or compositions which comprise them for use as antibacterial agents.

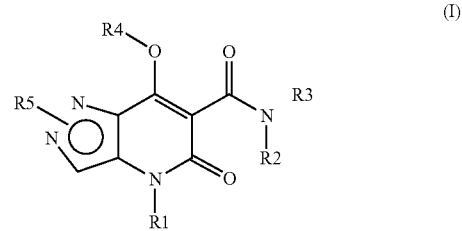

6 Claims, 1 Drawing Sheet

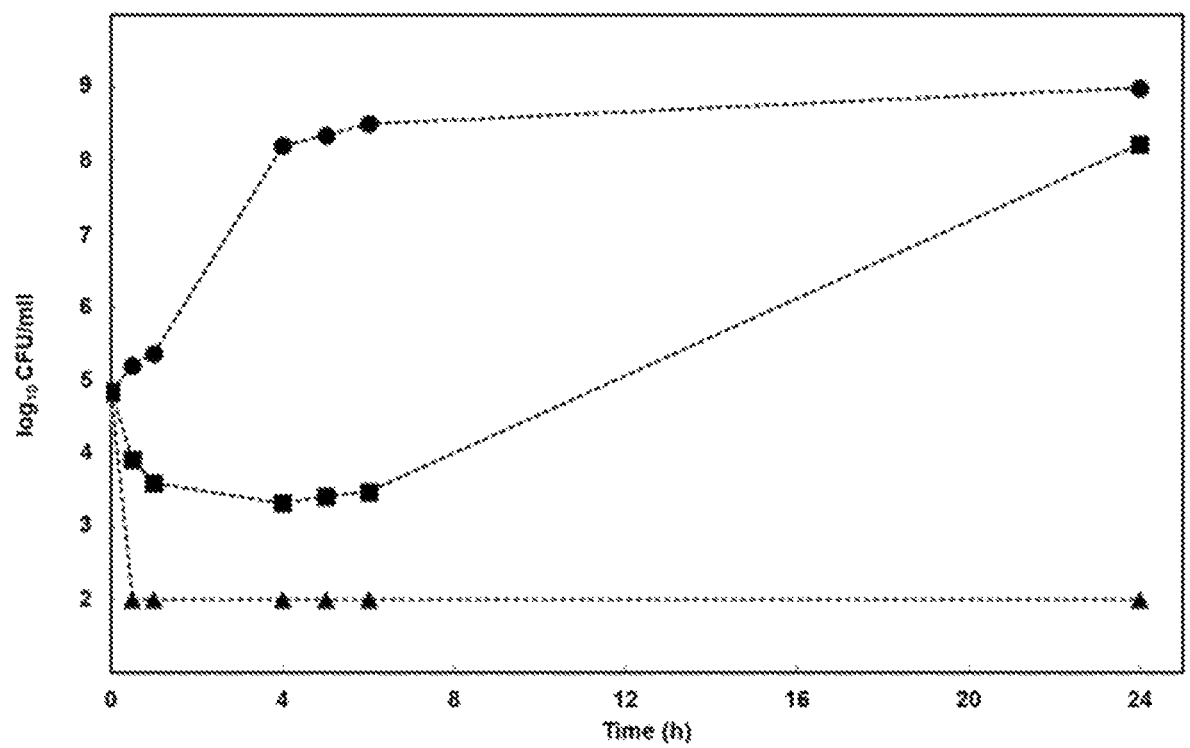

ANTIBACTERIAL COMPOUNDS

This application is a U.S. national stage of PCT/IB2020/055270 filed on 4 Jun. 2020 which claims priority to and the benefit of Italian patent application No. 102019000008151 filed on 5 Jun. 2019, the content of which are incorporated herein by reference in their entireties.

TECHNICAL FIELD

The present invention relates to compounds of formula (I)

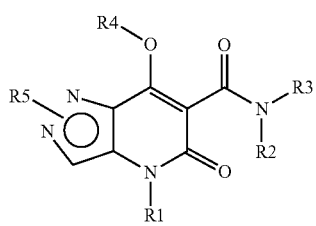

salts and derivatives thereof.

Further object of the present invention are compositions, which comprise at least a compound of formula (I) or its pharmaceutically acceptable salts and derivatives and excipients and, optionally, a further active compound.

Further object of the present invention are compounds of formula (I) or compositions which comprise them for use as antibacterial agents.

STATE OF ART

Bacterial resistance to currently available antibiotics is an increasingly frequent issue in both the hospital setting and the community.

Multi-drug or even pan-drug resistance, i.e. resistance to nearly all available antibiotic classes (e.g. beta-lactams, quinolones, tetracyclines, glycopeptides and macrolides) is rapidly emerging among the clinically relevant pathogenic bacteria, both Gram-positive and Gram-negative. This problem represents one of the most urgent medical need, as described for instance in O'Neil, J., 2014. Review on Antimicrobial Resistance, Antimicrobial Resistance: Tackling a Crisis for the Health and Wealth of Nations. doi: 10.1038/510015a; World Health Organization, 2014. Antimicrobial resistance: global report on surveillance 2014, World Health Organization. doi:9789241564748. The prevalence and severity of the antibiotic resistance (AR) phenomenon, which are associated with increased morbidity and mortality due to infectious disease, contribute to create a huge economic burden on Public Healthcare systems. Several Gram-negative bacteria were recently identified by the World Health Organization as "critical", in consideration of their rapid evolution towards multi-drug or even pan-drug resistance phenotypes and their relentless dissemination in the clinical setting. Such bacteria include *Acinetobacter baumannii, Pseudomonas aeruginosa* and Enterobacteriaceae (such as *Escherichia coli* and *Klebsiella pneumoniae*) (WHO document, "Global priority list of antibiotic resistant bacteria to guide research, discovery and development of new antibiotics", 27 Feb. 2017). This situation prompted the re-instatement of colistin, an old antibiotic, as a last-resort antibacterial therapy, which inevitably determined the worldwide spread of colistin-resistant clinical isolates (Biswas, S. et al. 2012. Colistin: an update on the antibiotic of the 21st century. Expert Rev. Anti-Infect. Ther. 10, 917-934. These isolates, showing pan-drug resistance phenotypes, cause extremely difficult-to-treat and life-threatening infections (Sherry N., Howden B., 2018, Emerging Gram negative resistance to last-line antimicrobial agents fosfomycin, colistin and ceftazidime-avibactam—epidemiology, laboratory detection and treatment implications, Expert Rev. Anti-Infect. Ther. 16:289-306.

There is thus an extremely urgent need to discover and develop new antibiotics, as well as to find new strategies that can restore the efficacy of already available antibiotics.

DESCRIPTION OF THE FIGURES

FIG. 1: bactericidal activity on *Acinetobacter baumannii* (N50 strain) of polymyxin E1, 2 mg/L (square); polymyxin E1, 2 mg/L+compound Ib 32 mg/L (triangles); control (circles).

DETAILED DESCRIPTION OF THE INVENTION

Herein, 4,5-dihydro-7-hydroxy-5-oxo-2H-pyrazolo[4,3-b]pyridin-6-carboxamides are described, which are active against several clinically relevant bacterial species, including those causing difficult-to-treat and life-threatening infections in relation to their broad resistance profile to currently available antibacterial drugs.

Compounds of general formula (I)

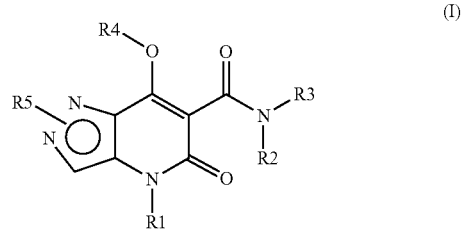

were used to generate a series of analogues, salts and prodrugs thereof, which show a potent direct-acting antibacterial activity and/or a potent synergistic activity with some commercially available antibacterial drugs. The present invention also relates to said compounds for use in the treatment of infectious diseases caused by Gram-positive and Gram-negative bacteria, either susceptible or resistant to currently available antibacterial drugs, as well as by protozoa, fungi and viruses, and pharmaceutical compositions comprising one or more of said compounds and methods of treatment with these pharmaceutical compositions.

Further object of the present invention is a composition comprising at least a compound of formula (I) and at least a further antibacterial agent.

Definitions

For the purposes of the present invention, the term "treatment" refers to any act intended to ameliorate the health status of a patient, such as therapy, prevention, prophylaxis and retardation of a disease, in particular a bacterial infection. In certain embodiments, such term refers to the amelioration or eradication of the disease, or symptoms associated with it. In other embodiments, this term refers to minimizing the spread or worsening of the disease, resulting from the administration of one or more therapeutic agents to a subject with such a disease.

As used herein, the terms "subject", "individual" or "patient" are interchangeable and refer to an animal, preferably to a mammal, and even more preferably to a human, including adult, child, newborn or at the prenatal stage. However, the term "subject" can also refer to non-human animals, in particular mammals such as dogs, cats, horses, cows, pigs, sheep and non-human primates, among others.

The terms "quantity" and "dose" are used interchangeably herein and may refer to an absolute quantification of a molecule.

The terms "active principle", "active ingredient" and "ingredient pharmaceutically active" are equivalent and refer to a component of a pharmaceutical composition having a therapeutic effect.

The term "therapeutic effect" refers to an effect induced by an active ingredient, or a pharmaceutical composition according to the present invention, able to prevent or to delay the appearance of a disease, or to cure or to attenuate the effects of a disease.

The term "effective amount" refers to a quantity of an active ingredient or of a pharmaceutical composition which prevents, removes or reduces the deleterious effects of the disease. It is obvious that the quantity to be administered can be adapted by the man skilled in the art according to the subject to be treated, to the nature of the disease, etc. In particular, doses and regimen of administration may be function of the nature, of the stage and of the severity of the disease to be treated, as well as of the weight, the age and the global health of the subject to be treated, as well as of the judgment of the doctor.

The term "excipient" refers to any ingredient, except active ingredients, that is present in a pharmaceutical composition. Its addition may be aimed to confer a particular consistency or other physical properties to the final product. An excipient must not be responsible for any interaction, in particular chemical, with the active ingredients.

A suitable pharmaceutically acceptable salt of a compound of the present invention which is sufficiently acidic is an alkali metal salt, for example a sodium or potassium salt, an alkaline earth metal salt, for example a calcium or magnesium salt, an ammonium salt or a salt with an organic base which affords a pharmaceutically acceptable cation, for example a salt with methylamine, dimethylamine, trimethylamine, piperidine, morpholine or tris-(2-hydroxyethyl) amine.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric centre, for example a carbon atom is bonded to four different groups, a pair of enantiomers is possible. An enantiomer can be characterized by the absolute configuration of its asymmetric centre, which can be defined as R- or S- according to the sequencing rules of Cahn-Ingold-Prelog, or by the manner in which the molecule rotates the plane of polarized light and designated as dextrorotatory or levorotatory (i.e., as (+) or (−)-isomer respectively). A chiral compound can exist as either individual enantiomer or as a mixture of two enantiomers. A mixture containing equal percentages of the two enantiomers is called a "racemic mixture".

The compounds, according to the present invention, are compounds of formula (I)

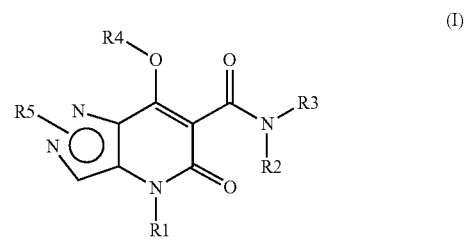

wherein,

R1, R5 are selected independently in the group comprising:
  H;
  linear or branched C1-C10 alkyl optionally containing 1-3 multiple bonds, carboxy, hydroxy, acyloxy, amino, halide, C1-C3 alkylamino, C1-C3 dialkylamino;
  C3-C7 cycloalkyl optionally containing heteroatoms such as N, O, S; aryl, arylalkyl, arylalkenyl optionally containing heterocyclic rings and substituted on the aromatic ring with halogen, C1-C3 alkyl, C1-C3 alkoxy, C1-C3 alkylthio, trifluoromethyl, methylenedioxy;

R2, R3 are selected independently in the group comprising:
  H;
  linear or branched C1-C6 alkyl;
  C3-C12 cycloalkyl optionally substituted with halogen, hydroxy, carboxy, amino;
  aryl, arylalkyl optionally containing heterocyclic rings and substituted on the aromatic ring with halogen, C1-C3 alkyl, C1-C3 alkoxy, C1-C3 alkylthio, trifluoromethyl, methylenedioxy;
  alternatively, R2, R3, form, together with the nitrogen atom to which they are bonded, a 5- to 7-membered heteroalicyclic ring;

R4 is selected in the group comprising:
  H;
  $Na^+$, $K^+$, $Cs^+$, $NMe_4^+$;
  Me, Et, n-Pr;
  $P(O)(OH)_2$, $P(O)(OMe)_2$, $P(O)(OEt)_2$, $P(O)(OPh)_2$, $P(O)(OCH_2Ph)_2$, $S(O)_2OH$, $S(O)_2NH_2$, $S(O)_2NMe_2$, C(O)H, C(O)Me, C(O)Et, C(O)Pr, $C(O)CH(Me)_2$, $C(O)C(Me)_3$, C(O)Ph, $C(O)CH_2Ph$, $CO_2Me$, $CO_2Et$, $CO_2CH_2Ph$, C(O)NHMe, $C(O)NMe_2$, C(O)NHEt, $C(O)NEt_2$, C(O)NHPh, $C(O)NHCH_2Ph$;
  acyl residues of C4-C10 carboxylic acids optionally containing 1-3 multiple bonds;
  acyl residues of the amino acids glycine, alanine, valine, leucine, isoleucine, serine, threonine, cysteine, methionine, proline, asparagine, glutamine, aspartic acid, glutamic acid, lysine, arginine, histidine, phenylalanine, tyrosine, and tryptophan.

In a preferred embodiment,
R1 is selected in the group comprising:
  C1-C6 linear or branched alkyl optionally containing carboxy, hydroxy, acyloxy, amino, C1-C3 alkylamino, C1-C3 dialkylamino;

C3-C5 cycloalkyl optionally containing heteroatoms such as N, O, S; arylalkyl optionally containing heterocyclic rings and substituted on the aromatic ring with halogen, C1-C3 alkyl, C1-C3 alkoxy, C1-C3 alkylthio, trifluoromethyl, methylenedioxy;

R2, R3 are selected independently in the group comprising
H;
linear or branched C1-C6 alkyl;
C6-C12 cycloalkyl optionally substituted with halogen, hydroxy, carboxy, amino;
aryl, arylalkyl optionally containing heterocyclic rings and substituted on the aromatic ring with halogen, C1-C3 alkyl, C1-C3 alkoxy, C1-C3 alkylthio, trifluoromethyl, methylenedioxy;
alternatively, R2, R3, form, together with the nitrogen atom to which they are bonded, a 5- to 7-membered heteroalicyclic ring;

R4 is selected in the group comprising:
H;
$Na^+$, $K^+$, $Cs^+$, $NMe_4^+$;
Me, Et, n-Pr;
$P(O)(OH)_2$, $P(O)(OMe)_2$, $P(O)(OEt)_2$, $P(O)(OPh)_2$, $P(O)(OCH_2Ph)_2$, $S(O)_2OH$, $S(O)_2NH_2$, $S(O)_2NMe_2$, C(O)H, C(O)Me, C(O)Et, C(O)Pr, $C(O)CH(Me)_2$, $C(O)C(Me)_3$, C(O)Ph, $C(O)CH_2Ph$, $CO_2Me$, $CO_2Et$, $CO_2CH_2Ph$, C(O)NHMe, $C(O)NMe_2$, C(O)NHEt, $C(O)NEt_2$, C(O)NHPh, $C(O)NHCH_2Ph$;
acyl residues of C4-C6 carboxylic acids optionally containing one multiple bond;
acyl residues of the amino acids glycine, alanine, valine, leucine, isoleucine, serine, threonine, cysteine, methionine, proline, asparagine, glutamine, aspartic acid, glutamic acid, lysine, arginine, histidine, phenylalanine, tyrosine, and tryptophan;

R5 is selected independently in the group comprising:
linear or branched C1-C6 alkyl optionally containing one multiple bond, carboxy, hydroxy, acyloxy, amino, C1-C3 alkylamino, C1-C3 dialkylamino;
C3-C5 cycloalkyl optionally containing heteroatoms such as N, O, S; aryl, arylalkyl, arylalkenyl optionally containing heterocyclic rings and substituted on the aromatic ring with halogen, C1-C3 alkyl, C1-C3 alkoxy, C1-C3 alkylthio, trifluoromethyl, methylenedioxy.

In another further preferred embodiment
R1, R5 are selected independently in the group comprising:
linear or branched C1-C5 alkyl optionally containing one multiple bond, carboxy, hydroxy, acyloxy, amino, C1-C3 alkylamino, C1-C3 dialkylamino;
C3-C5 cycloalkyl optionally containing heteroatoms such as N, O; aryl, arylalkyl optionally containing heterocyclic rings and substituted on the aromatic ring with halogen, methoxy, methylthio, trifluoromethyl;
R2, R3 are selected independently in the group comprising:
H;
C6-C12 cycloalkyl optionally substituted with halogen, hydroxy, carboxy, amino;
aryl, arylalkyl optionally containing heterocyclic rings and substituted on the aromatic ring with halogen, C1-C3 alkyl, C1-C3 alkoxy, C1-C3 alkylthio, trifluoromethyl, methylenedioxy;
alternatively, R2, R3, form, together with the nitrogen atom to which they are bonded, a 5- to 7-membered heteroalicyclic ring:

R4 is selected in the group comprising:
H;
$Na^+$, $K^+$, $Cs^+$, $NMe_4^+$;
Me, Et, n-Pr;
$P(O)(OH)_2$, $P(O)(OMe)_2$, $P(O)(OEt)_2$, $P(O)(OPh)_2$, $P(O)(OCH_2Ph)_2$, $S(O)_2OH$, $S(O)_2NH_2$, $S(O)_2NMe_2$, C(O)H, C(O)Me, C(O)Et, C(O)Pr, $C(O)CH(Me)_2$, $C(O)C(Me)_3$, C(O)Ph, $C(O)CH_2Ph$, $CO_2Me$, $CO_2Et$, $CO_2CH_2Ph$, C(O)NHMe, $C(O)NMe_2$, C(O)NHEt, $C(O)NEt_2$, C(O)NHPh, $C(O)NHCH_2Ph$;
acyl residues of C4-C6 carboxylic acids optionally containing one multiple bond;
acyl residues of the amino acids glycine, alanine, valine, leucine, isoleucine, serine, threonine, cysteine, methionine, proline, asparagine, glutamine, aspartic acid, glutamic acid, lysine, arginine, histidine, phenylalanine, tyrosine, and tryptophan.

In yet another preferred embodiment
R1 is selected in the group comprising:
linear or branched C1-C5 alkyl optionally containing one multiple bond, carboxy, hydroxy, acyloxy, amino, C1-C3 alkylamino, C1-C3 dialkylamino;
C3-C5 cycloalkyl optionally containing heteroatoms such as N, O; aryl, arylalkyl optionally containing heterocyclic rings and substituted on the aromatic ring with halogen, methoxy, methylthio, trifluoromethyl;
R2 is H;
R4 is H;
R5 is selected in the group comprising methyl, ethyl, isopropyl, 2-hydroxyethyl, 2-acetoxyethyl.

In yet another further embodiment, said compound is selected from among:
N-(adamantan-1-yl)-4-(1-butyl)-4,5-dihydro-7-hydroxy-2-methyl-5-oxo-2H-pyrazolo[4,3-b]pyridin-6-carboxamide,
4-(1-butyl)-4,5-dihydro-7-hydroxy-N-(1-hydroxyadamantan-3-yl)-2-methyl-5-oxo-2H-pyrazolo[4,3-b]pyridin-6-carboxamide,
N-(adamantan-1-yl)-4,5-dihydro-4-(4-fluoro-1-butyl)-7-hydroxy-2-methyl-5-oxo-2H-pyrazolo[4,3-b]pyridin-6-carboxamide,
4,5-dihydro-4-(4-fluoro-1-butyl)-7-hydroxy-N-(1-hydroxyadamantan-3-yl)-2-methyl-5-oxo-2H-pyrazolo[4,3-b]pyridin-6-carboxamide,
N-(adamantan-1-yl)-4,5-dihydro-7-hydroxy-2-methyl-5-oxo-4-(1-pentyl)-2H-pyrazolo[4,3-b]pyridin-6-carboxamide,
4-(4-acetoxy-1-butyl)-N-(adamantan-1-yl)-4,5-dihydro-7-hydroxy-2-methyl-5-oxo-2H-pyrazolo[4,3-b]pyridin-6-carboxamide,
N-(adamantan-1-yl)-4-(1-butyl)-4,5-dihydro-7-hydroxy-1-methyl-5-oxo-2H-pyrazolo[4,3-b]pyridin-6-carboxamide,
4-(1-butyl)-4,5-dihydro-7-hydroxy-N-(1-hydroxyadamantan-3-yl)-1-methyl-5-oxo-2H-pyrazolo[4,3-b]pyridin-6-carboxamide,
N-(adamantan-1-yl)-4,5-dihydro-4-(4-fluoro-1-butyl)-7-hydroxy-1-methyl-5-oxo-2H-pyrazolo[4,3-b]pyridin-6-carboxamide,
4,5-dihydro-4-(4-fluoro-1-butyl)-7-hydroxy-N-(1-hydroxyadamantan-3-yl)-1-methyl-5-oxo-2H-pyrazolo[4,3-b]pyridin-6-carboxamide, N-(adamantan-1-yl)-4,5-dihydro-7-hydroxy-1-methyl-5-oxo-4-(1-pentyl)-2H-pyrazolo[4,3-b]pyridin-6-carboxamide, N-(adamantan-1-yl)-4,5-dihydro-7-hydroxy-2-(2-hydroxyethyl)-5-oxo-4-(1-propyl)-2H-pyrazolo[4,3-b]pyridin-6-carboxamide, N-(adamantan-1-yl)-4-(1-butyl)-4,5-dihydro-7-hydroxy-2-(2-hydroxyethyl)-5-oxo-2H-pyrazolo[4,3-b]pyridin-6-carboxamide, N-(adamantan-1-yl)-4,5-dihydro-7-hydroxy-2-(2-hydroxyethyl)-5-oxo-4-(1-pentyl)-2H-pyrazolo[4,3-b]pyridin-6-carboxamide, 4,5-dihydro-7-hydroxy-N-(1-hydroxyadamantan-3-yl)-2-(2-hydroxyethyl)-5-oxo-4-(1-pentyl)-2H-pyrazolo[4,3-b]pyridin-6-carboxamide, N-(adamantan-1-yl)-4-(1-butyl)-4,5-dihydro-7-hydroxy-1-(2-hydroxyethyl)-5-oxo-2H-pyrazolo[4,3-b]pyridin-6-carboxamide, N-(adamantan-1-yl)-4,5-dihydro-7-hydroxy-4-(4-hydroxy-1-butyl)-2-methyl-5-oxo-2H-pyrazolo[4,3-b]pyridin-6-carboxamide, 2-(2-acetoxyethyl)-N-(adamantan-1-yl)-4,5-dihydro-7-hydroxy-5-oxo-4-(1-propyl)-2H-pyrazolo[4,3-b]pyridin-6-carboxamide, 4,5-dihydro-7-hydroxy-N-(1-hydroxyadamantan-3-yl)-1-methyl-5-oxo-4-(3-propenyl)-2H-pyrazolo[4,3-b]pyridin-6-carboxamide, 4-(1-butyl)-4,5-dihydro-N-(4-fluorobenzyl)-7-hydroxy-2-methyl-5-oxo-2H-pyrazolo[4,3-b]pyridin-6-carboxamide, 4-(1-butyl)-4,5-dihydro-N-(4-fluorophenyl)-7-hydroxy-2-methyl-5-oxo-2H-pyrazolo[4,3-b]pyridin-6-carboxamide, 4-(1-butyl)-N-[(1-tert-butoxycarbonyl-2-phenyl)ethan-1yl]-4,5-dihydro-7-hydroxy-2-methyl-5-oxo-2H-pyrazolo[4,3-b]pyridin-6-carboxamide, 4-(1-butyl)-N-cyclopentyl-4,5-dihydro-7-hydroxy-2-methyl-5-oxo-2H-pyrazolo[4,3-b]pyridin-6-carboxamide, 4-(1-butyl)-N-(tert-butyl)-4,5-dihydro-7-hydroxy-2-methyl-5-oxo-2H-pyrazolo[4,3-b]pyridin-6-carboxamide, 4-(1-butyl)-N-(tert-butyl)-4,5-dihydro-2-ethyl-7-hydroxy-5-oxo-2H-pyrazolo[4,3-b]pyridin-6-carboxamide, N-(adamantan-1-yl)-4-(1-butyl)-4,5-dihydro-2-ethyl-7-hydroxy-5-oxo-2H-pyrazolo[4,3-b]pyridin-6-carboxamide, 4-(1-butyl)-N-cyclooctyl-4,5-dihydro-7-hydroxy-2-methyl-5-oxo-2H-pyrazolo[4,3-b]pyridin-6-carboxamide, 4-(1-butyl)-4,5-dihydro-7-hydroxy-2-methyl-5-oxo-N-(1,2,3,4-tetrahydro-1-naphthyl)-2H-pyrazolo[4,3-b]pyridin-6-carboxamide, 4-(1-butyl)-4,5-dihydro-N-(diphenylmethyl)-7-hydroxy-2-methyl-5-oxo-2H-pyrazolo[4,3-b]pyridin-6-carboxamide, 4,5-dihydro-7-hydroxy-N-(1-hydroxyadamantan-3-yl)-2-methyl-5-oxo-4-(2-propyl)-2H-pyrazolo[4,3-b]pyridin-6-carboxamide, N-cyclooctyl-4,5-dihydro-7-hydroxy-2-methyl-5-oxo-4-(2-propyl)-2H-pyrazolo[4,3-b]pyridin-6-carboxamide, 4,5-dihydro-7-hydroxy-2-methyl-5-oxo-4-(2-propyl)-N-(1,2,3,4-tetrahydro-1-naphthyl)-2H-pyrazolo[4,3-b]pyridin-6-carboxamide, 4,5-dihydro-N-(diphenylmethyl)-7-hydroxy-2-methyl-5-oxo-4-(2-propyl)-2H-pyrazolo[4,3-b]pyridin-6-carboxamide, N-(adamantan-1-yl)-4,5-dihydro-7-hydroxy-2-methyl-5-oxo-4-(2-propyl)-2H-pyrazolo[4,3-b]pyridin-6-carboxamide, N-(adamantan-1-yl)-4,5-dihydro-7-methoxy-2-methyl-5-oxo-4-(1-pentyl)-2H-pyrazolo[4,3-b]pyridin-6-carboxamide, 7-acetoxy-N-(adamantan-1-yl)-4,5-dihydro-2-methyl-5-oxo-4-(1-propyl)-2H-pyrazolo[4,3-b]pyridin-6-carboxamide, N-(adamantan-1-yl)-4,5-dihydro-4-(4-fluoro-1-butyl)-7-(3-ethoxycarbonyl-1-oxopropoxy)-2-methyl-5-oxo-2H-pyrazolo[4,3-b]pyridin-6-carboxamide, N-(adamantan-1-yl)-4,5-dihydro-4-(4-fluoro-1-butyl)-7-(3-carboxy-1-oxopropoxy)-2-methyl-5-oxo-2H-pyrazolo[4,3-b]pyridin-6-carboxamide sodium salt, N-(adamantan-1-yl)-4-(1-butyl)-7-dibenzylphosphoryloxy-4,5-dihydro-2-ethyl-5-oxo-2H-pyrazolo[4,3-b]pyridin-6-carboxamide, N-(adamantan-1-yl)-4-(1-butyl)-4,5-dihydro-2-ethyl-5-oxo-7-phosphoryloxy-2H-pyrazolo[4,3-b]pyridin-6-carboxamide disodium salt.

The compounds of the present invention may possess one or more asymmetric centres; such compounds can therefore be produced as individual (R)- or (S)-stereoisomers or as mixtures thereof. Unless indicated otherwise, the description or nomenclature of a particular compound in the specification of the invention and in the claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic mixture. Some of the compounds of the invention may have geometric isomeric centres (E/Z-isomers). It is to be understood that the present invention encompasses all optical, diastereomeric and geometric isomers and mixtures thereof that possess antibacterial activity.

It is also to be understood that certain compounds of formula (I) may exist in solvated as well as unsolvated forms such as, for example, hydrated forms. It is to be understood that the present invention encompasses all said solvated forms.

It is also to be understood that certain compounds of formula (I) may exhibit polymorphism, and that the present invention encompasses all the polymorphs of said compounds.

The pyrazolo[4,3-b]pyridine-6-carboxamides compounds, object of the present specification, show both a direct and synergistic antibacterial activity on a variety of both Gram-positive and Gram-negative bacteria, including opportunistic pathogens responsible for life-threatening or difficult-to-treat infections.

The compounds according to the present invention surprisingly show a direct antibacterial activity on bacteria, such as *Bacillus subtilis, Enterococcus faecalis, Streptococcus pyogenes* and *Staphylococcus aureus*. Said compounds also exhibit synergistic antibacterial activity on Gram-negative bacteria, particularly with the antibiotic of the polymyxin class, such as polymyxin E1.

The present invention thus provides a method for inhibiting bacterial growth or killing bacterial cells when an effective amount of a compound, or a pharmaceutically acceptable salt, hydrate or solvate thereof, or a pharmaceutical composition as defined in the present specification, is used in combination with a suitable antibacterial drug.

The present invention also provides a method for the prevention or treatment of bacterial infection in a patient in need of such treatment; said method comprising administering to said patient a therapeutically effective amount of a compound, or a pharmaceutically acceptable salt, hydrate or solvate thereof, or a pharmaceutical composition as defined in the present specification, potentially in combination with a suitable antibacterial drug.

The compounds described in the present specification or the pharmaceutical composition comprising said compounds may be administered by any conventional route of administration. In particular, the compounds or the pharmaceutical composition described in the present specification can be administered by a topical, enteral, oral, parenteral, intranasal, intravenous, intra-arterial, intramuscular, intravesical, intraurethral, subcutaneous or intraocular administration and the like. In particular, the compounds or the pharmaceutical composition described in the present specification can be formulated for a topical, enteral, oral, parenteral, intranasal, intravenous, intra-arterial, intramuscular, subcutaneous or intraocular administration and the like.

Preferably, the compounds or the pharmaceutical composition described in the present specification are administered by enteral or parenteral route of administration. When administered parenterally, the compounds or the pharmaceutical composition described in the present specification are preferably administered by intravenous route of administration. When administered enterally, the compounds or the pharmaceutical composition described in the present specification are preferably administered by oral route of administration. When administered intravesically, the compounds or the pharmaceutical composition described in the present specification are preferably administered by intraurethral route of administration.

For oral administration, the pharmaceutical composition can be formulated into conventional dosage forms such as tablets, capsules, powders, granules and liquid preparations such as syrups, elixirs, and concentrated drops. Nontoxic solid excipients or diluents may be included in the pharmaceutical composition, such as, for example, mannitol, lactose, starch, magnesium stearate, sodium saccharine, talcum, cellulose, glucose, sucrose, magnesium, carbonate, and the like. For compressed tablets, aggregants or binders, which are agents which impart cohesive qualities to powdered materials, may be also used. For example, starch, gelatin, sugars such as lactose or dextrose, and natural or synthetic gums can be used as binders.

Disintegrants are also necessary in the case of tablets or pills to facilitate break-up of the tablet. Disintegrants include starches, clays, celluloses, algins, gums and crosslinked polymers. Moreover, lubricants and glidants are also included in the pharmaceutical preparation to prevent adhesion of the tablet material to surfaces in the manufacturing process and to improve the flow characteristics of the powder material during manufacture. Colloidal silicon dioxide is commonly used as a glidant, while compounds such as talc or stearic acids are commonly used as lubricants.

For transdermal administration, the pharmaceutical composition can be formulated into ointment, cream or gel form and can contain appropriate penetrants or detergents to facilitate permeation of the active ingredient, such as dimethylsulfoxide, dimethylacetamide and dimethylformamide.

For transmucosal administration, nasal sprays, or vaginal or rectal suppositories can be used. The active ingredient can be incorporated into any of the suppository bases already known and widely described in the art. Examples of such bases include cocoa butter, polyethylene glycols (carbowaxes), polyethylene sorbitan monostearate, and mixtures thereof or any other compatible material used to modify the melting point or dissolution rate.

Pharmaceutical compositions according to the present specification may be formulated to release the active ingredient either substantially immediately upon administration or at any predetermined time or time period after administration. The compounds or the pharmaceutical composition according to the present specification may be administered as a single dose or in multiple doses. Preferably, the treatment is administered regularly, preferably between daily and monthly, or preferably between daily and weekly. In a particular embodiment, the treatment is administered several times a day, preferably 2 or 3 times a day, even more preferably 3 times a day.

The duration of treatment with the compound according to the present invention or the pharmaceutical composition according to the present invention is preferably comprised between 1 day and 20 weeks, or preferably between 5 days and 10 weeks, or still more preferably between 5 days and 4 weeks, or even more preferably between 5 days and 2 weeks. In a particular embodiment, the duration of the treatment is of at least 1 week. Alternatively, the treatment may last as long as the bacterial infection persists.

The amount of compound according to the present invention or of pharmaceutical composition according to the present invention to be administered has to be determined by standard procedure well known by those of ordinary skills in the art. Physiological data of the patient (e.g. age, size, and weight) and the routes of administration have to be taken into account to determine the appropriate dosage, so as a therapeutically effective amount will be administered to the patient.

The nature or the form of the pharmaceutical compositions, the route of administration and the dose of administration of the compound according to the present invention, or the pharmaceutical composition according to the present invention can be adjusted by the man skilled in the art according to the type and severity of the disease, and to the state of the patient, in particular his/her/its age, weight, sex, or general physical condition.

In a further embodiment, the present invention describes and claims the use of compounds or pharmaceutical compositions according to the present invention in methods of antimicrobial susceptibility testing, in order to determine the phenotype of sensitivity or resistance to individual compounds or combinations thereof. For this purpose and purely by way of example, methods of the prior art are used such as microdilution in broth, diffusion on agar.

The present invention will now be described in more detail by the following examples, which are included in order to disclose some embodiments of the invention, but not in any way to limit the scope of the invention.

Chemical Synthesis

The novel 4,5-dihydro-7-hydroxy-5-oxo-2H-pyrazolo[4,3-b]pyridin-6-carboxamide compounds according to the invention can be prepared by methods which are similar to those described in the literature for the preparation of quinolone analogues, such as e.g. laquinimod (Björk, A. et al., Quinoline derivatives. WO00003991, Jan. 27, 2000, Active Biotech AB; Jönsson, S. et al., Synthesis and Biological Evaluation of New 1,2-Dihydro-4-hydroxy-2-oxo-3-quinolinecarboxamides for Treatment of Autoimmune Disorders: Structure-Activity Relationship. J. Med. Chem. 2004, 47, 2075-2088; Matsuo, M. et al., Quinoline derivatives. WO9218483, Oct. 29, 1992, Fujisawa Pharmaceutical Co. Ltd.) or thieno[2,3-b]piridone analogues (Björk, A. and Jansson, K., Thienopyridone carboxamides and their medical use. WO2005123744, Dec. 29, 2005, Active Biotech AB). Thus, carboxamides (a) can be prepared by reacting acid derivatives (b), activated by e.g. DCC- or HBTU-coupling procedure, or by reacting ester derivatives (c) with either aliphatic or aromatic amines (d), or by reacting N,N-disubstituted amides (e) with aromatic amines at high temperatures (Scheme 1). The carboxylic acids (b) can be prepared by acidic hydrolysis of the ester derivatives (c).

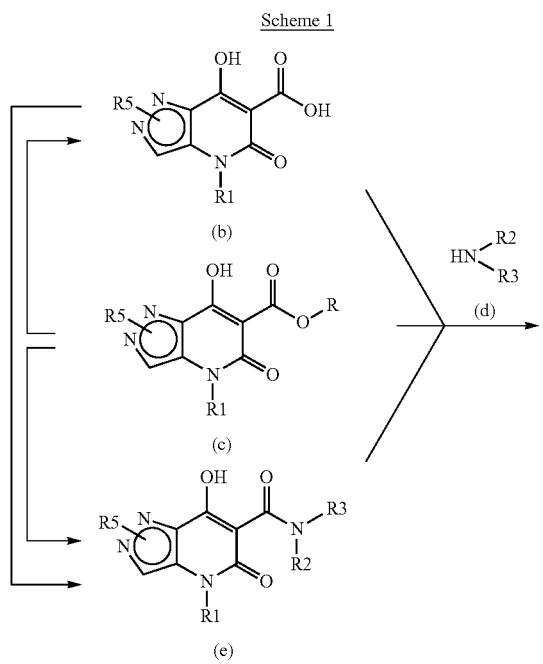

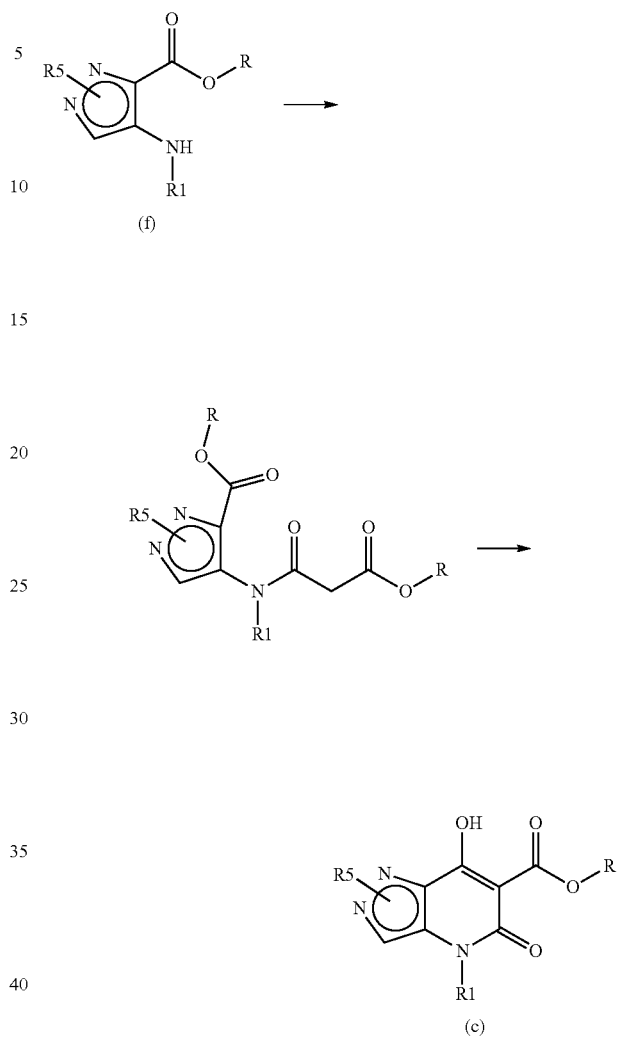

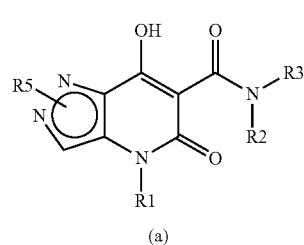

The preparation of the ester derivatives (c) was usually performed by reacting a suitably substituted aminopyrazole-carboxylate (f) with alkyl 3-chloro-3-oxopropionate followed by Dieckmann condensation under basic conditions to obtain the esters (c). The basic conditions referred to in the above reactions require typically a strong non-nucleophilic base, such as NaH, in an aprotic solvent, such as toluene or THF or mixtures of them, in presence of catalytic amount of an alcohol at temperatures 40-120° C.

In the preparations of esters (c) described above, the R1 group may be included in the starting materials as shown, or, alternatively, it may be introduced in a last step. Thus, the aminopyrazole derivatives (g) by reaction with alkyl 3-chloro-3-oxopropionate provided the malonamido derivatives (h), which were subjected to NH protection as e.g. Boc derivatives (i). These underwent cyclization under basic condition to yield the pyrazolo[4,3-b]pyridinone esters (j), which were deprotected by treatment with mild acids to the corresponding derivatives (k). Subsequent alkylation/arylation of these intermediates gave the esters (c) (Scheme 3). The experimental conditions of the above reactions are typically an alkyl halide and a strong non-nucleophilic base, such as NaH, in an aprotic solvent, such as DMF at temperatures 20-120° C. for the alkylation reactions, and an aryl/heroaryl halide or boronic acid in presence of a metal catalyst, such as copper or palladium, in an aprotic solvent, such as DMF at temperatures 20-120° C. for the arylation reactions.

Scheme 3

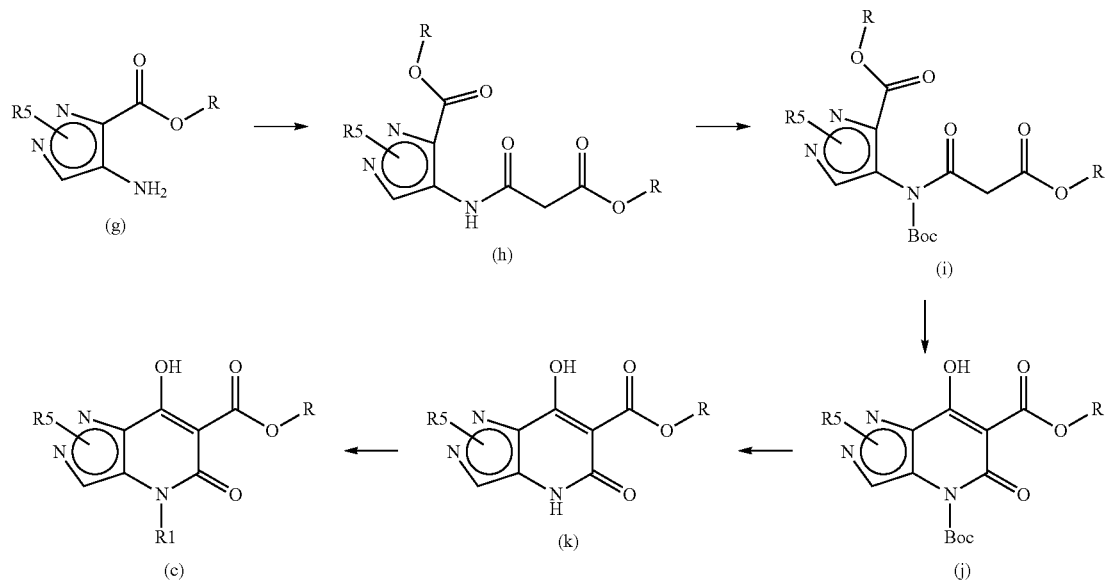

Aminopyrazole derivatives (f) bearing the R1 substituent can be prepared starting from aminopyrazoles (g) by reaction with: i. alkyl halides in aprotic solvents, such as DMF; ii. alkyl halides in presence of a non-nucleophilic base, such as sodium, potassium, cesium (bi)carbonate or a trialkylamine, in aprotic solvents, such as DMF, acetone or acetonitrile; iii. aliphatic or aromatic carbonyl compounds and a suitable reducing agent, such as sodium borohydride, sodium triacetoxyborohydride, sodium cyanoborohydride, in the presence of an acidic catalyst (p-toluenesulfonic acid, acetic acid, boric acid); iv. arylboronic acids and copper(I) iodide in aprotic solvents, typically DMF (Scheme 4).

Scheme 4

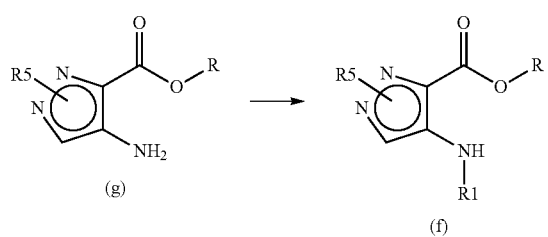

Aminopyrazole derivatives compounds (g) are commercially available or can be prepared according to known procedures (La Rosa, S. et al., Fused 3-Hydroxy-3-trifluoromethylpyrazoles Inhibit Mutant Huntingtin Toxicity. ACS Med. Chem. Lett. 2013, 4, 979-984; Regiec, A. et al., Methylation of 4-nitro-3(5)-pyrazolecarboxylic acid. Tetrahedron Lett. 2009, 50, 2624-2627; Squarcialupi, L. et al., Structural refinement of pyrazolo[4,3-d]pyrimidine derivatives to obtain highly potent and selective antagonists for the human A3 adenosine receptor. Eur. J. Med. Chem. 2016, 108, 117-133; McCoull, W. et al., Identification of pyrazolopyrimidinones as GHS-R1a antagonists and inverse agonists for the treatment of obesity. Med Chem Comm 2013, 4, 456-462; Lenzi, O. et al., 2-Phenylpyrazolo[4,3-d]pyrimidin-7-one as a new scaffold to obtain potent and selective human A3 adenosine receptor antagonists: new insights into the receptor-antagonist recognition. J. Med. Chem. 2009, 52, 7640-7652).

Preparation of the 4-acyloxy (I) prodrug compounds from (a) can be performed using activated acid derivatives, such as acid chlorides or anhydrides, and a non-nucleophilic base, such as trialkylamine, in non-nucleophilic solvents, such as $CH_2Cl_2$.

Scheme 5

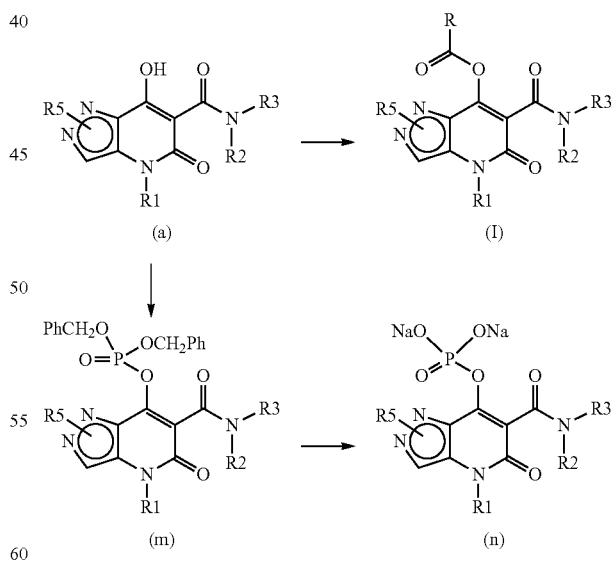

Preparation of the 4-phosphoryloxy (m) prodrug compounds can be performed using either dibenzyl chlorophosphite, generated in situ from $(PhCH_2O)_2POH$ and $CCl_4$, and a non-nucleophilic base, such as trialkylamine, in non-nucleophilic solvents, such as $CH_3CN$, or tetrabenzyl pyrophosphate $[(PhCH_2O)_2PO]_2O$ and a non-nucleophilic base, such as trialkylamine, in non-nucleophilic solvents, such as CH₂Cl₂ or a stronger base, such as NaH or LDA, in non-nucleophilic solvents, such as THF or CH₂Cl₂ (Scheme 5). The phosphoryloxy compound di-sodium salt (n) can be prepared by hydrogenolysis of (m) in presence of Na₂CO₃ or NaOH in protic solvents, such as alcohols with low boiling point (Scheme 5).

Example 1.1

4-(1-Butyl)-4,5-dihydro-7-hydroxy-N-(1-hydroxy-adamantan-3-yl)-2-methyl-5-oxo-2H-pyrazolo[4,3-b]pyridin-6-carboxamide (Ia)

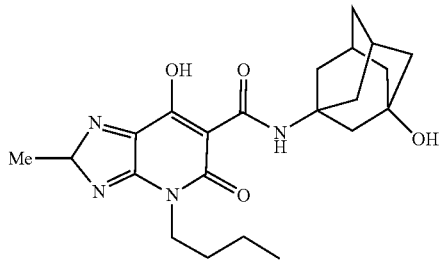 [SMILES: CCCCn1c(=O)c(C(=O)NC23CC4CC(CC(O)(C4)C2)C3)c(O)c2c1=NC(C)N=2]

A solution of 3-[N-(1-butyl)-N-[3-(methoxycarbonyl)-1-methyl-1H-pyrazol-4-yl]amino]-3-oxopropanoic acid methyl ester (298.6 mg, 0.96 mmol) in anhydrous THF (35 mL) was added dropwise to a suspension of 60% sodium hydride (77 mg, 1.92 mmol) in the same solvent (20 mL) containing dry methanol (20 µL, 0.48 mmol). The reaction mixture was stirred at 60° C. for 2 h, then evaporated to leave a solid residue which was taken up into 5% sodium carbonate solution. The aqueous solution was extracted with diethyl ether to remove some starting material, then brought to pH 1 by adding 6 N HCl and extracted with ethyl acetate (3×20 mL). The organic layer was dried over anhydrous sodium sulfate, filtered, and evaporated to give the Dieckmann condensation product methyl 4-(1-butyl)-4,5-dihydro-7-hydroxy-2-methyl-5-oxo-2H-pyrazolo[4,3-b]pyridin-6-carboxylate as a solid residue insoluble in most organic solvents, which was used in the next step without further purification.

A mixture of methyl 4-(1-butyl)-4,5-dihydro-7-hydroxy-2-methyl-5-oxo-2H-pyrazolo[4,3-b]pyridin-6-carboxylate (0.96 mmol), 3-aminoadamantan-1-ol (321.1 mg, 1.92 mmol) in THF (3 mL) and toluene (10 mL) was refluxed for 1-2 h, while adding dropwise further toluene and distilling out the azeotropic mixture methanol/toluene. After completion of the reaction, solvent was removed under reduced pressure and the solid residue was taken up into ethyl acetate. The organic solution was washed successively with 2 N HCl and brine, then dried over anhydrous sodium sulphate, filtered, and concentrated to yield a solid residue which was purified by recrystallization from ethyl acetate to give the title compound (178.8 mg, 45%) as white needle-like solid; mp 216-218° C.

¹H NMR (400 MHz, CDCl₃): δ 18.61 and 17.47 (s, 1H), 11.41 and 10.32 (s, 1H), 7.26 and 7.23 (s, 1H), 4.02 (s, 3H), 3.83-3.79 (m, 2H), 2.23 (s, 2H), 2.07 (s, 2H), 1.97-1.94 (m, 2H), 1.69-1.46 (m, 11H), 1.36-1.27 (m, 2H), 0.88 (t, J=7.3 Hz, 3H).

MS (ESI) m/z 415 [M+H]⁺.

Other compounds prepared according to Example 1.1 are reported in Table 1.

TABLE 1

| Example | Chemical name | Melting point (° C.) |
|---|---|---|
| 1.2 | N-(Adamantan-1-yl)-4-(1-butyl)-4,5-dihydro-7-hydroxy-2-methyl-5-oxo-2H-pyrazolo[4,3-b]pyridin-6-carboxamide (Ib) | 101-105 |
| 1.3 | N-(Adamantan-1-yl)-4,5-dihydro-4-(4-fluoro-1-butyl)-7-hydroxy-2-methyl-5-oxo-2H-pyrazolo[4,3-b]pyridin-6-carboxamide (Ic) | 191-192 |
| 1.4 | 4,5-Dihydro-4-(4-fluoro-1-butyl)-7-hydroxy-N-(1-hydroxyadamantan-3-yl)-2-methyl-5-oxo-2H-pyrazolo[4,3-b]pyridin-6-carboxamide (Id) | 209-211 |
| 1.5 | N-(Adamantan-1-yl)-4,5-dihydro-7-hydroxy-2-methyl-5-oxo-4-(1-pentyl)-2H-pyrazolo[4,3-b]pyridin-6-carboxamide (Ie) | 151-153 |
| 1.6 | 4-(4-Acetoxy-1-butyl)-N-(adamantan-1-yl)-4,5-dihydro-7-hydroxy-2-methyl-5-oxo-2H-pyrazolo[4,3-b]pyridin-6-carboxamide (If) | 209-210 |
| 1.7 | N-(Adamantan-1-yl)-4-(1-butyl)-4,5-dihydro-7-hydroxy-1-methyl-5-oxo-2H-pyrazolo[4,3-b]pyridin-6-carboxamide (Ig) | 131-134 |
| 1.8 | 4-(1-Butyl)-4,5-dihydro-7-hydroxy-N-(1-hydroxyadamantan-3-yl)-1-methyl-5-oxo-2H-pyrazolo[4,3-b]pyridin-6-carboxamide (Ih) | 95-96 |
| 1.9 | N-(Adamantan-1-yl)-4,5-dihydro-4-(4-fluoro-1-butyl)-7-hydroxy-1-methyl-5-oxo-2H-pyrazolo[4,3-b]pyridin-6-carboxamide (Ii) | 148-149 |
| 1.10 | 4,5-Dihydro-4-(4-fluoro-1-butyl)-7-hydroxy-N-(1-hydroxyadamantan-3-yl)-1-methyl-5-oxo-2H-pyrazolo[4,3-b]pyridin-6-carboxamide (Ij) | 132-133 |
| 1.11 | N-(Adamantan-1-yl)-4,5-dihydro-7-hydroxy-1-methyl-5-oxo-4-(1-pentyl)-2H-pyrazolo[4,3-b]pyridin-6-carboxamide (Ik) | 126-128 |
| 1.12 | N-(Adamantan-1-yl)-4,5-dihydro-7-hydroxy-2-(2-hydroxyethyl)-5-oxo-4-(1-propyl)-2H-pyrazolo[4,3-b]pyridin-6-carboxamide (Il) | 133-135 |
| 1.13 | N-(Adamantan-1-yl)-4-(1-butyl)-4,5-dihydro-7-hydroxy-2-(2-hydroxyethyl)-5-oxo-2H-pyrazolo[4,3-b]pyridin-6-carboxamide (Im) | 204-205 |
| 1.14 | N-(Adamantan-1-yl)-4,5-dihydro-7-hydroxy-2-(2-hydroxyethyl)-5-oxo-4-(1-pentyl)-2H-pyrazolo[4,3-b]pyridin-6-carboxamide (In) | 156-157 |
| 1.15 | 4,5-Dihydro-7-hydroxy-N-(1-hydroxyadamantan-3-yl)-2-(2-hydroxyethyl)-5-oxo-4-(1-pentyl)-2H-pyrazolo[4,3-b]pyridin-6-carboxamide (Io) | 144-147 |
| 1.16 | N-(Adamantan-1-yl)-4-(1-butyl)-4,5-dihydro-7-hydroxy-1-(2-hydroxyethyl)-5-oxo-2H-pyrazolo[4,3-b]pyridin-6-carboxamide (Ip) | 96-98 |
| 1.17 | N-(Adamantan-1-yl)-4,5-dihydro-7-hydroxy-4-(4-hydroxy-1-butyl)-2-methyl-5-oxo-2H-pyrazolo[4,3-b]pyridin-6-carboxamide (Iq) | glassy solid |

TABLE 1-continued

| Example | Chemical name | Melting point (° C.) |
|---|---|---|
| 1.18 | 2-(2-Acetoxyethyl)-N-(adamantan-1-yl)-4,5-dihydro-7-hydroxy-5-oxo-4-(1-propyl)-2H-pyrazolo[4,3-b]pyridin-6-carboxamide (Ir) | 168-169 |
| 1.19 | 4-(1-Butyl)-N-cyclooctyl-4,5-dihydro-7-hydroxy-2-methyl-5-oxo-2H-pyrazolo[4,3-b]pyridin-6-carboxamide (Is) | 179-181 |
| 1.20 | 4-(1-Butyl)-4,5-dihydro-7-hydroxy-2-methyl-5-oxo-N-(1,2,3,4-tetrahydro-1-naphthyl)-2H-pyrazolo[4,3-b]pyridin-6-carboxamide (It) | 180-182 |
| 1.21 | 4-(1-Butyl)-4,5-dihydro-N-(diphenylmethyl)-7-hydroxy-2-methyl-5-oxo-2H-pyrazolo[4,3-b]pyridin-6-carboxamide (Iu) | 173-176 |
| 1.22 | N-(Adamantan-1-yl)-4-(1-butyl)-4,5-dihydro-2-ethyl-7-hydroxy-5-oxo-2H-pyrazolo[4,3-b]pyridin-6-carboxamide (Iv) | 155-158 |
| 1.23 | 4-(1-Butyl)-4,5-dihydro-N-(1,1-dimethylethyl)-2-ethyl-7-hydroxy-5-oxo-2H-pyrazolo[4,3-b]pyridin-6-carboxamide (Iw) | 152-154 |
| 1.24 | N-(Adamantan-1-yl)-4,5-dihydro-7-hydroxy-2-methyl-5-oxo-4-(2-propyl)-2H-pyrazolo[4,3-b]pyridin-6-carboxamide (Ix) | 266-270 |
| 1.25 | 4,5-Dihydro-7-hydroxy-N-(1-hydroxyadamantan-3-yl)-2-methyl-5-oxo-4-(2-propyl)-2H-pyrazolo[4,3-b]pyridin-6-carboxamide (Iy) | >280 |
| 1.26 | N-Cyclooctyl-4,5-dihydro-7-hydroxy-2-methyl-5-oxo-4-(2-propyl)-2H-pyrazolo[4,3-b]pyridin-6-carboxamide (Iz) | 187-191 |
| 1.27 | 4,5-Dihydro-7-hydroxy-2-methyl-5-oxo-4-(2-propyl)-N-(1,2,3,4-tetrahydro-1-naphthyl)-2H-pyrazolo[4,3-b]pyridin-6-carboxamide (Iaa) | 214-216 |
| 1.28 | 4,5-Dihydro-N-(diphenylmethyl)-7-hydroxy-2-methyl-5-oxo-4-(2-propyl)-2H-pyrazolo[4,3-b]pyridin-6-carboxamide (Iab) | 205-208 |
| 1.29 | 4-(1-Butyl)-4,5-dihydro-N-[(4-fluorophenyl)methyl]-7-hydroxy-2-methyl-5-oxo-2H-pyrazolo[4,3-b]pyridin-6-carboxamide (Iac) | 177-181 |
| 1.30 | 1,1-Dimethylethyl (S)-2-[4-(1-butyl)-4,5-dihydro-7-hydroxy-2-methyl-5-oxo-2H-pyrazolo[4,3-b]pyridin-6-carboxamido]-3-phenylpropanoate (Iad) | amorphous solid |
| 1.31 | 4-(1-Butyl)-4,5-dihydro-N-(4-fluorophenyl)-7-hydroxy-2-methyl-5-oxo-2H-pyrazolo[4,3-b]pyridin-6-carboxamide (Iae) | 190-192 |
| 1.32 | 4-(1-Butyl)-4,5-dihydro-N-(1,1-dimethylethyl)-7-hydroxy-2-methyl-5-oxo-2H-pyrazolo[4,3-b]pyridin-6-carboxamide (Iaf) | 173-176 |
| 1.33 | 4-(1-Butyl)-N-cyclopentyl-4,5-dihydro-7-hydroxy-2-methyl-5-oxo-2H-pyrazolo-[4,3-b]pyridin-6-carboxamide (Iag) | 155-159 |

Example 2.1

3-[N-(1-Butyl)-N-[3-(methoxycarbonyl)-1-methyl-1H-pyrazol-4-yl]amino]-3-oxopropanoic acid methyl ester

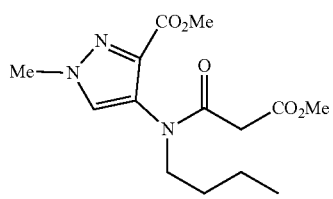 [SMILES: CCCCN(C(=O)CC(=O)OC)c1cn(C)nc1C(=O)OC]

A solution of methyl 3-chloro-3-oxopropionate (0.12 mL, 1.11 mmol) in dry dichloromethane (2-3 mL) was added dropwise to an ice-cooled solution of methyl 4-(1-butylamino)-1-methyl-1H-pyrazole-3-carboxylate (156 mg, 0.74 mmol) and triethylamine (0.15 mL, 1.11 mmol) in dry dichloromethane (10 mL). After stirring at rt for 2 h, the solution was washed with saturated solution of sodium hydrogen carbonate, then 2 N HCl and brine. The organic layer was dried over anhydrous sodium sulphate and evaporated to give an oily residue, which was purified by flash column chromatography on silica gel. Elution with ethyl acetate/petroleum ether (2:1) yielded the title compound (172.6 mg, 75%) as a light yellow oil.

$^1$H NMR (400 MHz, CDCl$_3$): δ 7.37 (s, 1H), 3.91 (s, 3H), 3.82 (s, 3H), 3.58 (s, 3H), 3.22-3.15 (m, 3H), 1.39-1.32 (m, 2H), 1.26-1.17 (m, 2H), 0.80 (t, J=7.3 Hz, 3H).

MS (ESI): m/z 312 [M+H]$^+$, 334 [M+Na]$^+$.

Other compounds prepared according to Example 2.1 are reported in Table 2.

TABLE 2

| Example | Chemical name | Physical properties |
|---|---|---|
| 2.2 | 3-[N-(4-Fluoro-1-butyl)-N-[3-(methoxycarbonyl)-1-methyl-1H-pyrazol-4-yl]amino]-3-oxopropanoic Acid Methyl Ester | light yellow oil |
| 2.3 | 3-[N-[3-(Methoxycarbonyl)-1-methyl-1H-pyrazol-4-yl]-N-(1-pentyl)]amino]-3-oxopropanoic Acid Methyl Ester | light yellow oil |
| 2.4 | 3-[N-(4-Acetoxy-1-butyl)-N-[3-(methoxycarbonyl)-1-methyl-1H-pyrazol-4-yl]amino]-3-oxopropanoic Acid Methyl Ester | light yellow oil |
| 2.5 | 3-[N-(1-Butyl)-N-[5-(methoxycarbonyl)-1-methyl-1H-pyrazol-4-yl]amino]-3-oxopropanoic Acid Methyl Ester | light yellow oil |
| 2.6 | 3-[N-(4-Fluoro-1-butyl)-N-[5-(methoxycarbonyl)-1-methyl-1H-pyrazol-4-yl]amino]-3-oxopropanoic Acid Methyl Ester | light yellow oil |
| 2.7 | 3-[N-[5-(Methoxycarbonyl)-1-methyl-1H-pyrazol-4-yl]-N-(1-pentyl)-amino]-3-oxopropanoic Acid Methyl Ester | light yellow oil |

TABLE 2-continued

| Example | Chemical name | Physical properties |
|---|---|---|
| 2.8 | 3-[N-[1-(2-Acetoxyethyl)-3-(methoxycarbonyl)-1H-pyrazol-4-yl]-N-(1-propyl)-amino]-3-oxopropanoic Acid Methyl Ester | light yellow solid, mp 73-75° C. |
| 2.9 | 3-[N-[1-(2-Acetoxyethyl)-3-(methoxycarbonyl)-1H-pyrazol-4-yl]-N-(1-butyl)-amino]-3-oxopropanoic Acid Methyl Ester | light yellow oil |
| 2.10 | 3-[N-[1-(2-Acetoxyethyl)-3-(methoxycarbonyl)-1H-pyrazol-4-yl]-N-(1-pentyl)-amino]-3-oxopropanoic Acid Methyl Ester | light yellow oil |
| 2.11 | 3-[N-[1-(2-Acetoxyethyl)-5-(methoxycarbonyl)-1H-pyrazol-4-yl]-N-(1-butyl)-amino]-3-oxopropanoic Acid Methyl Ester | light yellow oil |

Example 3.1

Methyl 4-(1-butylamino)-1-methyl-1H-pyrazole-3-carboxylate

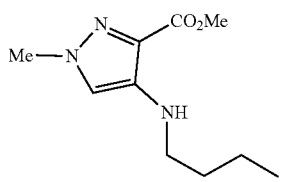

1-Iodobutane (416 mg, 2.26 mmol) was added to a solution of methyl 4-amino-1-methyl-1H-pyrazole-3-carboxylate (350 mg, 2.26 mmol) in dry DMF (3 mL) under a nitrogen atmosphere. The solution was gradually warmed to 50° C. and maintained at this temperature for 7 h. After cooling to rt, the solution was diluted with water (20 mL) and extracted with ethyl acetate. The organic layer was washed with 5% lithium chloride solution (4×10 mL), water (2×10 mL), then brine, and was dried over anhydrous sodium sulphate. Removal of solvent gave an oily residue, which was purified by flash column chromatography on silica gel (petroleum ether/ethyl acetate, 1:1, as eluent) to provide the title compound as a reddish oil; yield, 34%.

$^1$H NMR (400 MHz, CDCl$_3$): δ 6.74 (s, 1H), 4.70 (br s, 1H), 3.82 (s, 3H), 3.79 (s, 3H), 2.91 (t, J=7.0 Hz, 2H), 1.55-1.48 (m, 2H), 1.38-1.28 (m, 2H), 0.86 (t, J=7.3 Hz, 3H).

MS (ESI): m/z 234 [M+Na]$^+$.

Other compounds prepared according to Example 3.1 are reported in Table 3.

Biological Activity

Growth inhibition or killing of bacteria was investigated using conventional methods widely described in the scientific literature. Parameters such as the Minimum Inhibitory Concentration (MIC) were determined as described in Clinical Laboratory Standard Institute (CLSI) document M07 "Methods for Dilution Antimicrobial Susceptibility Tests for Bacteria That Grow Aerobically, 11th Edition" (2018). Synergistic activity of the compounds described in the present specification were determined by measuring the variation of the MIC's compound in the absence and presence of a sub-inhibitory concentration of a suitable antibacterial agent, such as polymyxin E1. Furthermore, the Fractional Inhibitory Concentrations (FICs) were measured using a chequerboard analysis to determine the average FIC index (FICI), whose value is known to characterize the interaction between two compounds and/or drugs (≤0.5, synergistic interaction; >0.5 and <2, no interaction, additive effect; ≥2, antagonistic interaction). Furthermore, the selectivity of the compounds was investigated by measuring their cytotoxic effect on mammalian cell lines (e.g. HeLa cells).

Example 4

Evaluation of the Direct-Acting Antibacterial Activity of pyrazolo[4,3-b]pyridin-6-carboxamides The MIC values were determined using the broth microdilution method as described in document M07 using Mueller-Hinton broth as culture medium and an initial bacterial inoculum size of 5×10$^5$ CFU/mL, with a final volume of 100 μL per well in a 96-well microplate. Bacterial strains were *Bacillus subtilis* ATCC 6633, *Enterococcus faecalis* ATCC 29212, *Streptococcus pyogenes* ATCC 12344 and *Staphylococcus aureus* ATCC 25923. The tested compound concentration ranged from 512 to 0.25 mg/L. Plates were incubated

TABLE 3

| Example | Chemical name | Physical properties |
|---|---|---|
| 3.2 | Methyl 4-[(4-Fluoro-1-butyl)amino]-1-methyl-1H-pyrazole-3-carboxylate | yellow oil |
| 3.3 | Methyl 1-Methyl-4-(1-pentylamino)-1H-pyrazole-3-carboxylate | yellow oil |
| 3.4 | Methyl 4-[(4-Acetoxy-1-butyl)amino]-1-methyl-1H-pyrazole-3-carboxylate | yellow oil |
| 3.5 | Methyl 4-(1-Butylamino)-1-methyl-1H-pyrazole-5-carboxylate | yellow oil |
| 3.6 | Methyl 4-[(4-Fluoro-1-butyl)amino]-1-methyl-1H-pyrazole-3-carboxylate | yellow oil |
| 3.7 | Methyl 1-Methyl-4-(1-pentylamino)-1H-pyrazole-5-carboxylate | yellow oil |
| 3.8 | Methyl 1-(2-Acetoxyethyl)-4-(1-propylamino)-1H-pyrazole-3-carboxylate | white crystals; mp 42-45° C. |
| 3.9 | Methyl 1-(2-Acetoxyethyl)-4-(1-butylamino)-1H-pyrazole-3-carboxylate | yellow oil |
| 3.10 | Methyl 1-(2-Acetoxyethyl)-4-(1-pentylamino)-1H-pyrazole-3-carboxylate | yellow oil |
| 3.11 | Methyl 1-(2-Acetoxyethyl)-4-(1-butylamino)-1H-pyrazole-5-carboxylate | yellow oil | for 18-24 hours at 35±2° C. prior to results analysis. The results are reported in table 4. As shown in the table, many compounds showed direct antibacterial activity, with MIC values as low as 16 or 32 mg/L.

TABLE 4

| | MIC (mg/L) | | | |
|---|---|---|---|---|
| Compound | S. pyogenes ATCC 12344 | B. subtilis ATCC 6633 | E. faecalis ATCC 29212 | S. aureus ATCC 25923 |
| Ib | 16 | 32 | 64 | 64 |
| Iac | 32 | 64 | 64 | 128 |
| Iad | 64 | 32 | 128 | 256 |
| Iae | 32 | 128 | 32 | 128 |
| Iaf | 64 | 128 | 512 | 64 |
| Ix | 32 | 64 | 32 | 128 |
| Iz | 16 | 32 | 64 | 32 |
| Iaa | 32 | 16 | 64 | 64 |
| Iab | 32 | 16 | 32 | 32 |
| It | 64 | 32 | 64 | 32 |
| Is | 32 | 32 | 512 | 32 |

Example 5

Evaluation of the Synergistic Antibacterial Activity of pyrazolo[4,3-b]pyridin-6-carboxamides Several methods were used to investigate the synergistic activity of the compounds, including (a) the determination of the MIC in the presence of a sub-inhibitory concentration of a suitable antibacterial agent, (b) the determination of the average FICI using a chequerboard analysis and (c) the time-kill curve analysis of a suitable agent (at a sub-inhibitory concentration) in the absence and presence of the pyrazolo[4,3-b]pyridin-6-carboxamide compound at a fixed concentration of 2 or 8 mg/L.

Example 5.1

Determination of the Potentiation Fold by Comparing the Compounds MIC Determined in the Absence and Presence of a Suitable Antibacterial Agent The MIC of the compound was determined alone and in the presence of a fixed and sub-inhibitory concentration of a suitable antibacterial agent of the polymyxin class, such as polymyxin E1 (colistin). The potentiation fold was computed as the ratio $MIC_{compound}/MIC_{compound+polymyxin\ E}$. Tested organisms included Escherichia coli $CCUG^T$ Klebsiella pneumoniae ATCC 13833 and Acinetobacter baumannii ATCC 17978, which show a colistin MIC of 0.5, 0.5 and 1 mg/L, respectively.

Table 5 reports the MIC values of tested compounds alone and in the presence of 0.25×MIC polymyxin E1 (i.e., at a fixed concentration of 0.12 mg/L, for Escherichia coli $CCUG^T$ and Klebsiella pneumoniae ATCC 13833 and of 0.25 mg/L for Acinetobacter baumannii ATCC 17978). Most compounds showed a significant decrease of the compound MIC in the presence of polymyxin E1, indicating an important potentiation effect (potentiation fold, up to ≥128).

TABLE 5

| | MIC (mg/L) | | | MIC (mg/L) in presence of colistin | | | Potentiation fold | | |
|---|---|---|---|---|---|---|---|---|---|
| Compound | E. coli $CCUG^T$ | K. pneumoniae ATCC 13833 | A. baumannii ATCC 17978 | E. coli $CCUG^T$ | K. pneumoniae ATCC 13833 | A. baumannii ATCC 17978 | E. coli $CCUG^T$ | K. pneumoniae ATCC 13833 | A. baumannii ATCC 17978 |
| Ir | >512 | >512 | >512 | 64 | 64 | 32 | ≥8 | ≥8 | ≥16 |
| Ib | >512 | >512 | >512 | 8 | 8 | 4 | ≥64 | ≥64 | ≥128 |
| Im | >512 | >512 | >512 | — | 8 | 8 | — | ≥64 | ≥64 |
| Ia | >512 | >512 | >512 | 32 | 64 | 32 | ≥16 | ≥8 | ≥16 |
| Ih | >512 | >512 | >512 | 64 | 32 | 32 | ≥8 | ≥16 | ≥16 |
| Ip | >512 | >512 | >512 | 32 | 16 | 32 | ≥16 | ≥32 | ≥16 |
| In | >512 | >512 | >512 | 64 | 16 | 32 | ≥8 | ≥32 | ≥16 |
| Io | >512 | >512 | >512 | — | 8 | 4 | — | ≥64 | ≥128 |
| Iad | >512 | >512 | >512 | 32 | 32 | 128 | ≥16 | ≥16 | ≥4 |
| Iae | >512 | >512 | >512 | 256 | 256 | 32 | ≥2 | ≥2 | ≥16 |
| Iaf | >512 | >512 | >512 | 32 | 32 | 64 | ≥16 | ≥16 | ≥8 |
| Iag | >512 | >512 | >512 | 32 | 64 | 128 | ≥16 | ≥8 | ≥4 |
| Iw | >512 | >512 | >512 | 16 | 32 | 64 | ≥32 | ≥16 | ≥8 |
| Ix | >512 | >512 | >512 | 8 | 8 | 8 | ≥64 | ≥64 | ≥64 |
| Iz | >512 | >512 | >512 | 8 | 16 | 8 | ≥64 | ≥32 | ≥64 |
| Iaa | >512 | >512 | >512 | 16 | 32 | 16 | ≥32 | ≥16 | ≥32 |
| Iab | >512 | >512 | >512 | 16 | 16 | 16 | ≥32 | ≥32 | ≥32 |
| It | >512 | >512 | >512 | 32 | 16 | 16 | ≥16 | ≥32 | ≥32 |
| Is | >512 | >512 | >512 | 32 | 32 | 32 | ≥16 | ≥16 | ≥16 |
| Iu | >512 | >512 | >512 | 64 | 64 | 32 | ≥8 | ≥8 | ≥16 |

Example 5.2

Determination of Average FIC Index by Chequerboard Analysis

"Chequerboard" method was used to further investigate the synergistic activity of pyrazolo[4,3-b]pyridin-6-carboxamides when this compounds are combined with polymyxin E1. The chequerboard analysis is a two-dimensional array in which individual microplate wells contain a unique combination of the concentrations of the tested compound and polymyxin E1. Tested concentrations of the compound ranged 64 to 0.06 mg/L along the x-axis, while polymyxin E1 concentrations ranged 32-0.5 mg/L (or 256-4 mg/L when polymyxin E1-resistant clinical isolates were used) and varied along the y-axis.

Determining the Fractional Inhibitory Concentration (FIC) of both compounds allows to calculate the average FIC index (FICI) and to analyse whether a synergistic activity (average FIC index equal to or minor than 0.5) between two compounds is observed (European Committee on Antimicrobial Susceptibility Testing EUCAST document "Terminology relating to methods for the determination of susceptibility of bacteria to antimicrobial agents, 2010). The results obtained are reported in table 6. A polymyxin E1-resistant *Acinetobacter baumannii* (strain N50) clinical isolate was used in this example (D'Andrea M. M. et al., Characterization of pABVA01, a plasmid encoding the OXA-24 carbapenemase from Italian isolates of *Acinetobacter baumannii*. Antimicrob. Agents Chemother. 2009, 53, 3528-3533. doi: 10.1128/AAC.00178-09).

TABLE 6

| MIC (mg/L) | | FIC | | | Average FIC |
|---|---|---|---|---|---|
| Compound | Colistin | Compound | Colistin | FIC index | index |
| 1024 | — | 1 | — | | |
| 64 | 0.5 | 0.0625 | 0.0625 | 0.1250 | |
| 32 | 2 | 0.0313 | 0.25 | 0.2813 | 0.303 |
| 4 | 4 | 0.0039 | 0.5 | 0.5039 | |
| — | 8 | — | 1 | | |

Table 7 shows the results of the chequerboard analysis (average FIC index) aimed at investigating the interaction between pyrazolo[4,3-b]pyridin-6-carboxamides and polymyxin E1 on several bacterial strains, including clinical strains resistant to antibiotics and in particular colistin.

TABLE 7

| Compound | Bacterial strain | Average FIC index |
|---|---|---|
| Ib | *E. coli* CCUG$^T$ | 0.26 |
| | *K. pneumoniae* ATCC 13833 | 0.30 |
| | *A. baumannii* ATCC 17978 | 0.29 |
| | *A. baumannii* N50[a] | 0.30 |
| Im | *K. pneumoniae* SI-4B[a] | 0.31 |
| | *K. pneumoniae* SI-27[a] | 0.41 |
| In | *K. pneumoniae* ATCC 13833 | 0.32 |
| Ip | *K. pneumoniae* ATCC 13833 | 0.32 |
| | *E. coli* CCUG$^T$ | 0.33 |
| Ix | *K. pneumoniae* ATCC 13833 | 0.33 |
| | *A. baumannii* ATCC 17978 | 0.27 |
| | *K. pneumoniae* SI-4B[a] | 0.39 |

[a]strains resistant to colistin (MIC polymyxin E1 ≥ 4 mg/L)

As shown in Tables 6 and 7, all computed average FIC index values are significantly below 0.5, ranging 0.26-0.41, indicating a strong synergistic activity of the pyrazolo[4,3-b]pyridin-6-carboxamides with polymyxin E1. Interestingly, the synergism with polymyxin E1 was observed with both susceptible reference strains and resistant clinical isolates of *Acinetobacter baumannii* and *Klebsiella pneumoniae*.

Example 5.3

Time-Kill Curve Analysis to Evaluate the Bactericidal Activity of Colistin in Combination with the Compounds The kinetics of bacterial killing offers an additional mean to characterize the antibacterial activity of compounds, also in combination with other antimicrobial agents. Compounds or a combination thereof are defined as bactericides when the viable bacterial load is decreased by at least 3 $\log_{10}$ (EUCAST, cit.).

This analysis was carried with a multidrug-resistant *Acinetobacter baumannii* clinical isolate showing resistance to polymyxin E1. The time-kill curves were generated starting from a bacterial inoculum of $10^5$ CFU/mL. Bacterial count was determined at several time intervals in the absence (control) or presence of 2 mg/L polymyxin E1 (corresponding to the resistance breakpoint, EUCAST, cit.) supplemented with 32 mg/L of compound Ib (FIG. 1).

The curves shown in FIG. 1 clearly show how polymyxin E1 is unable to achieve complete and irreversible killing of the bacterial population at a drug concentration equivalent to the resistance breakpoint, in clear relation to the resistance phenotype of the bacterial strain used. However, it is equally clear that a composition that comprises 2 mg/L of polymyxin E1 and compound Ib at a concentration of 32 mg/L, shows an extremely rapid and potent bactericidal activity, with a reduction in the bacterial viable count of more than 3 log 10 already observable after 30-60 min of incubation, and no viable could be detected at subsequent time intervals up to 24 hours. These data support the bactericidal activity of pyrazolo[4,3-b]pyridin-6-carboxamides compounds on Gram-negative bacteria, when combined with sub-inhibitory concentrations of polymyxin E1.

Example 6

Evaluation of the Cytotoxicity of pyrazolo[4,3-b]pyridin-6-carboxamides on Eukaryotic Cells (Selectivity)

The selectivity and potential cytotoxic effect of antibacterial compounds is a key aspect of such drugs. These aspects could be investigated with several methods, including cell membrane integrity assays on in vitro cultures of eukaryotic (human) cells exposed to various concentrations of the compound. Considering the synergistic activity of the compounds described in the present specification, including in the presence of polymyxin E1, such experiments were carried with the compound alone and with the compound in presence of a fixed concentration of polymyxin E1 (512 mg/L).

Selected compounds were tested for their ability to induce the lysis of eukaryotic cells by measuring the release of lactate dehydrogenase enzyme (LDH), a cytoplastic enzyme, from HeLa cells, after incubating such cells for 24 hours (37° C., 5% CO2) in Dulbecco's modified Eagle medium supplemented with 10% foetal bovine serum, 4.5 mg/mL glucose and 2 mM L-glutamine in the absence and presence of the compound at concentrations ranging from 0.001 to 1.2 mM. LDH activity was determined using commercial kits (such as the CytoTox 96® Non-Radioactive Cytotoxicity Assay, Promega, Madison, Wisconsin, U.S.A.) in the samples, containing HeLa cells incubated with the various concentrations of the assayed compound or with the solvent or buffer used to resuspend such compounds (vehicle control). Further controls included samples containing the medium only (medium control) or in which cell lysis was induced by the addition of 9% Triton X-100 (maximum LDH release control). The percentage of cytotoxicity was computed as 100×(Sample LDH release)/(maximum LDH release). The variation of the percentage of cytotoxicity is usually dependent on the compound concentration and allowed to compute an $IC_{50}$ value, corresponding to the compound concentration inducing 50% cytotoxicity.

By using this procedure, the potential cytotoxic activity of compound Ib was tested at concentrations ranging 8-256 mg/L. The compound Ib appeared to have no cytotoxicity up to the maximum concentration tested ($IC_{50}$ values>256 mg/L). Interestingly, the $IC_{50}$ value of compound Ib was not modified either when (a) the experiment was performed in the presence of 512 mg/L of polymyxin E1 or (b) when the cell culture was incubated with the compound for up to 72 hours.

The invention claimed is:
1. A Compound of formula (I)

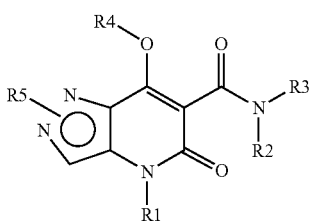

(I)

or a pharmaceutically acceptable salt thereof, wherein
R1, R5 are selected independently from the group consisting of:
  H;
  linear or branched C1-C10 alkyl optionally containing 1-3 multiple bonds, carboxy, hydroxy, acyloxy, amino, halide, C1-C3 alkylamino, C1-C3 dialkylamino;
  C3-C7 cycloalkyl optionally containing heteroatoms such as N, O, S; aryl, arylalkyl, arylalkenyl optionally containing heterocyclic rings and substituted on the aromatic ring with halogen, C1-C3 alkyl, C1-C3 alkoxy, C1-C3 alkylthio, trifluoromethyl, and methylenedioxy;
R2, R3 are selected independently from the group consisting of:
  H;
  linear or branched C1-C6 alkyl;
  C3-C12 cycloalkyl optionally substituted with halogen, hydroxy, carboxy, amino;
  aryl, arylalkyl, optionally containing heterocyclic rings and substituted on the aromatic ring with halogen, C1-C3 alkyl, C1-C3 alkoxy, C1-C3 alkylthio, trifluoromethyl, and methylenedioxy;
  alternatively, R2, R3, form, together with the nitrogen atom to which they are bonded, a 5- to 7-membered heteroalicyclic ring; and R4 is selected from the group consisting of:
  H;
  $Na^+$, $K^+$, $Cs^+$, $NMe_4^+$;
  Me, Et, n-Pr;
  $P(O)(OH)_2$, $P(O)(OMe)_2$, $P(O)(OEt)_2$, $P(O)(OPh)_2$, $P(O)(OCH_2Ph)_2$, $S(O)_2OH$, $S(O)_2NH_2$, $S(O)_2NMe_2$, C(O)H, C(O)Me, C(O)Et, C(O)Pr, $C(O)CH(Me)_2$, $C(O)C(Me)_3$, C(O)Ph, $C(O)CH_2Ph$, $CO_2Me$, $CO_2Et$, $CO_2CH_2Ph$, C(O)NHMe, $C(O)NMe_2$, C(O)NHEt, $C(O)NEt_2$, C(O)NHPh, $C(O)NHCH_2Ph$;
  acyl residues of C4-C10 carboxylic acids optionally containing 1-3 multiple bonds;
  acyl residues of the amino acids glycine, alanine, valine, leucine, isoleucine, serine, threonine, cysteine, methionine, proline, asparagine, glutamine, aspartic acid, glutamic acid, lysine, arginine, histidine, phenylalanine, tyrosine, and tryptophan,
wherein said compound is selected from the group consisting of:
N-(adamantan-1-yl)-4-(1-butyl)-4,5-dihydro-7-hydroxy-2-methyl-5-oxo-2H-pyrazolo [4,3-b]pyridin-6-carboxamide,
4-(1-butyl)-4,5-dihydro-7-hydroxy-N-(1-hydroxyadamantan-3-yl)-2-methyl-5-oxo-2H-pyrazolo [4,3-b]pyridin-6-carboxamide,
N-(adamantan-1-yl)-4,5-dihydro-4-(4-fluoro-1-butyl)-7-hydroxy-2-methyl-5-oxo-2H-pyrazolo [4,3-b]pyridin-6-carboxamide,
4,5-dihydro-4-(4-fluoro-1-butyl)-7-hydroxy-N-(1-hydroxyadamantan-3-yl)-2-methyl-5-oxo-2H-pyrazolo [4,3-b]pyridin-6-carboxamide,
N-(adamantan-1-yl)-4,5-dihydro-7-hydroxy-2-methyl-5-oxo-4-(1-pentyl)-2H-pyrazolo [4,3-b]pyridin-6-carboxamide,
4-(4-acetoxy-1-butyl)-N-(adamantan-1-yl)-4,5-dihydro-7-hydroxy-2-methyl-5-oxo-2H-pyrazolo [4,3-b]pyridin-6-carboxamide,
N-(adamantan-1-yl)-4-(1-butyl)-4,5-dihydro-7-hydroxy-1-methyl-5-oxo-2H-pyrazolo [4,3-b]pyridin-6-carboxamide,
4-(1-butyl)-4,5-dihydro-7-hydroxy-N-(1-hydroxyadamantan-3-yl)-1-methyl-5-oxo-2H-pyrazolo [4,3-b]pyridin-6-carboxamide,
N-(adamantan-1-yl)-4,5-dihydro-4-(4-fluoro-1-butyl)-7-hydroxy-1-methyl-5-oxo-2H-pyrazolo [4,3-b]pyridin-6-carboxamide,
4,5-dihydro-4-(4-fluoro-1-butyl)-7-hydroxy-N-(1-hydroxyadamantan-3-yl)-1-methyl-5-oxo-2H-pyrazolo [4,3-b]pyridin-6-carboxamide,
N-(adamantan-1-yl)-4,5-dihydro-7-hydroxy-1-methyl-5-oxo-4-(1-pentyl)-2H-pyrazolo [4,3-b]pyridin-6-carboxamide,
N-(adamantan-1-yl)-4,5-dihydro-7-hydroxy-2-(2-hydroxyethyl)-5-oxo-4-(1-propyl)-2H-pyrazolo [4,3-b]pyridin-6-carboxamide,
N-(adamantan-1-yl)-4-(1-butyl)-4,5-dihydro-7-hydroxy-2-(2-hydroxyethyl)-5-oxo-2H-pyrazolo [4,3-b]pyridin-6-carboxamide,
N-(adamantan-1-yl)-4,5-dihydro-7-hydroxy-2-(2-hydroxyethyl)-5-oxo-4-(1-pentyl)-2H-pyrazolo [4,3-b]pyridin-6-carboxamide,
4,5-dihydro-7-hydroxy-N-(1-hydroxyadamantan-3-yl)-2-(2-hydroxyethyl)-5-oxo-4-(1-pentyl)-2H-pyrazolo [4,3-b]pyridin-6-carboxamide,
N-(adamantan-1-yl)-4-(1-butyl)-4,5-dihydro-7-hydroxy-1-(2-hydroxyethyl)-5-oxo-2H-pyrazolo [4,3-b]pyridin-6-carboxamide, N-(adamantan-1-yl)-4,5-dihydro-7-hydroxy-4-(4-hydroxy-1-butyl)-2-methyl-5-oxo-2H-pyrazolo [4,3-b]pyridin-6-carboxamide, 2-(2-acetoxyethyl)-N-(adamantan-1-yl)-4,5-dihydro-7-hydroxy-5-oxo-4-(1-propyl)-2H-pyrazolo [4,3-b]pyridin-6-carboxamide, 4,5-dihydro-7-hydroxy-N-(1-hydroxyadamantan-3-yl)-1-methyl-5-oxo-4-(3-propenyl)-2H-pyrazolo [4,3-b]pyridin-6-carboxamide, N-(adamantan-1-yl)-4-(1-butyl)-4,5-dihydro-2-ethyl-7-hydroxy-5-oxo-2H-pyrazolo [4,3-b]pyridin-6-carboxamide, 4,5-dihydro-7-hydroxy-N-(1-hydroxyadamantan-3-yl)-2-methyl-5-oxo-4-(2-propyl)-2H-pyrazolo [4,3-b]pyridin-6-carboxamide, N-(adamantan-1-yl)-4,5-dihydro-7-hydroxy-2-methyl-5-oxo-4-(2-propyl)-2H-pyrazolo [4,3-b]pyridin-6-carboxamide, N-(adamantan-1-yl)-4,5-dihydro-7-methoxy-2-methyl-5-oxo-4-(1-pentyl)-2H-pyrazolo [4,3-b]pyridin-6-carboxamide, 7-acetoxy-N-(adamantan-1-yl)-4,5-dihydro-2-methyl-5-oxo-4-(1-propyl)-2H-pyrazolo [4,3-b]pyridin-6-carboxamide, N-(adamantan-1-yl)-4,5-dihydro-4-(4-fluoro-1-butyl)-7-(3-ethoxycarbonyl-1-oxopropoxy)-2-methyl-5-oxo-2H-pyrazolo [4,3-b]pyridin-6-carboxamide, N-(adamantan-1-yl)-4,5-dihydro-4-(4-fluoro-1-butyl)-7-(3-carboxy-1-oxopropoxy)-2-methyl-5-oxo-2H-pyrazolo [4,3-b]pyridin-6-carboxamide sodium salt, N-(adamantan-1-yl)-4-(1-butyl)-7-dibenzylphosphoryloxy-4,5-dihydro-2-ethyl-5-oxo-2H-pyrazolo [4,3-b]pyridin-6-carboxamide, and N-(adamantan-1-yl)-4-(1-butyl)-4,5-dihydro-2-ethyl-5-oxo-7-phosphoryloxy-2H-pyrazolo [4,3-b]pyridin-6-carboxamide disodium salt.

2. A pharmaceutical composition comprising at least one of the compounds according to claim 1, its pharmaceutically acceptable salts or solvates and excipients.

3. The pharmaceutical composition according to claim 2, further comprising one or more additional active compounds selected from among bactericidal and/or bacteriostatic agents.

4. The pharmaceutical composition according to claim 3, wherein said bactericidal and/or bacteriostatic agents are selected from the group of polymyxins.

5. Method of ameliorating, retarding or eradicating bacterial infections in patients in need thereof with the composition according to claim 4, said method comprising administering to said patients a therapeutically effective amount of said composition according to claim 4.

6. Method of ameliorating, retarding or eradicating gram positive bacterial infections in patients in need thereof with at least one compound according to claim 1, or salts or solvates thereof, said method comprising administering to said patients a therapeutically effective amount of said at least one compound according to claim 1, or said salts or said solvates.

\* \* \* \* \*